ROSE PLANT
Filed Dec. 10, 1952 2 Sheets-Sheet 1
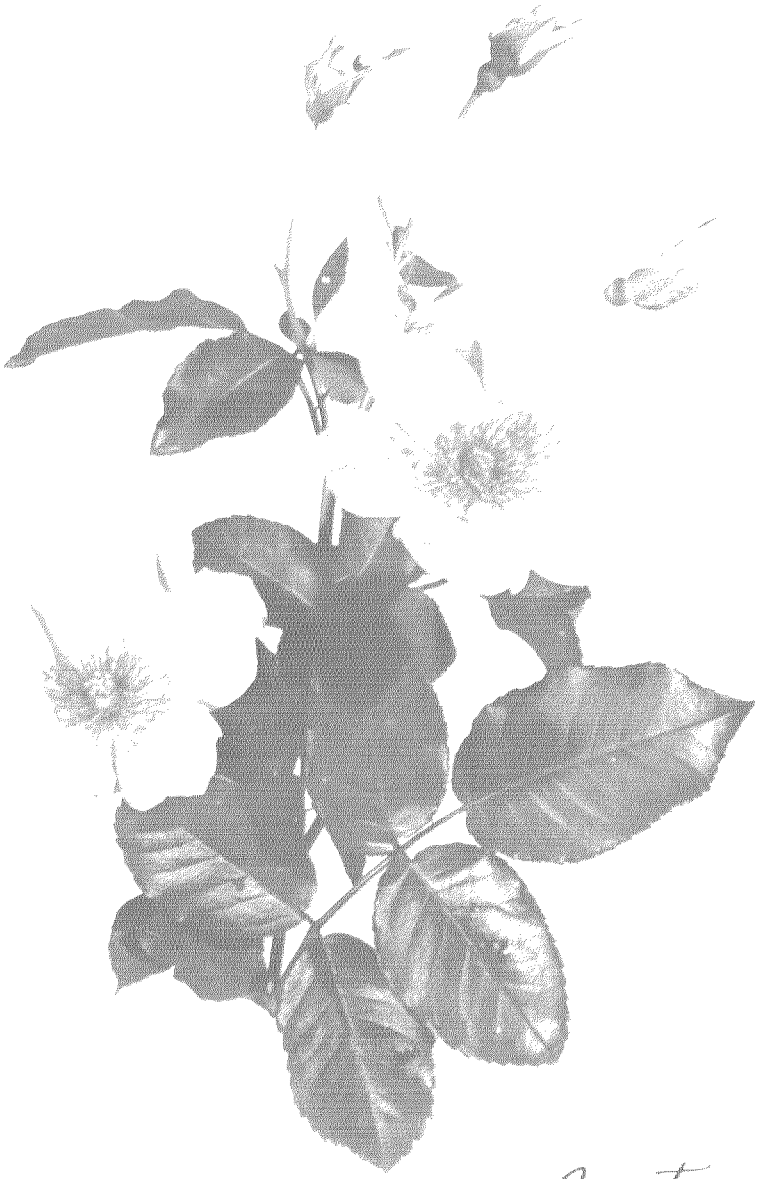
Inventor.
W. E. Lammerts
By: Robb & Robb
Attorneys ROSE PLANT
Filed Dec. 10, 1952 2 Sheets-Sheet 2
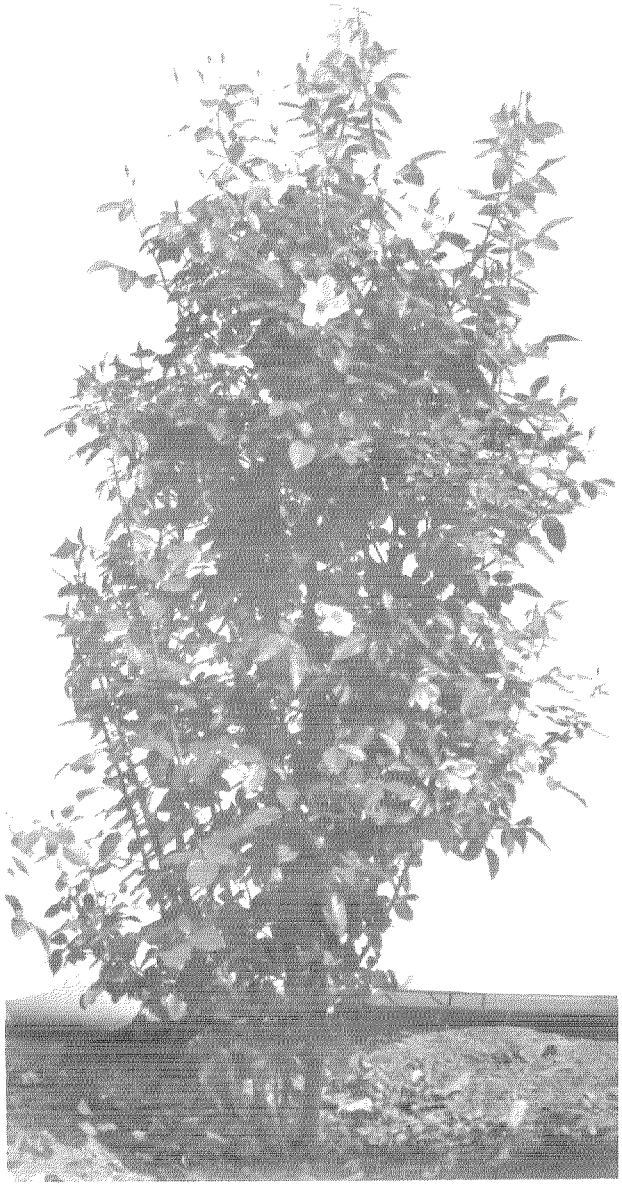
Inventor
W. E. Lammerts
By: Cobb & Cook
Attorneys Patented Jan. 5, 1954

Plant Pat. 1,239

UNITED STATES PATENT OFFICE 1,239

ROSE PLANT

Walter E. Lammerts, La Canada, Calif., assignor to Descanso Distributors, Inc., La Canada, Calif., a corporation of California Application December 10, 1952, Serial No. 325,245

1 Claim. (Cl. 47—61)

The present invention relates to a new and distinct variety of rose plant of the hybrid Wichuraiana class which was originated by me by crossing the variety "Crimson Glory" (Plant Patent No. 105) with the variety of "Captain Thomas" (Plant Patent No. 393).

As the result of this cross, I have produced a new variety of rose which is uniquely distinguished from its parents, as well as from all other varieties of its class, as evidenced by the following combination of dominant characteristics:

(1) Large, single flowers usually consisting of five petals and rarely having any petaloids, as distinguished from the parent variety "Captain Thomas" which usually has from two to four petaloids;

(2) The remarkably uniformly colored flowers having a general color tonality of deep lemon yellow in the fully open flowers, while the buds are the darkest shade of buttercup yellow, the flowers being much darker in color than the parent "Captain Thomas," and being more like the color of the double-flowering variety "High Noon" (Plant Patent No. 794);

(3) The very bushy, compact shrub or pillar rose habit of growth of the plant makes this new variety ideally suited for garden use, it being much more bush-like than "Captain Thomas," although eventually attaining a height of eight feet or more;

(4) The stems and leaves of the new variety are remarkably free from anthocyanin pigment, and accordingly have practically no reddish or bronze coloration as is characteristic of the variety "Captain Thomas";

(5) The buds of the new variety are also completely free of the reddish coloration that is characteristic of "Captain Thomas," and only rarely does the margin of one of the petals show a trace of light red color;

(6) The peduncle and stems of the new variety are much less pubescent and more glabrous than those of "Captain Thomas";

(7) The foliage is very abundant and affords very good coverage in this shrub, and the leaves are more flat and less wrinkled than those of "Captain Thomas," thereby producing an improved appearance which is still further enhanced by the large size of the dark green leaves;

(8) The relative freedom from thorns and the glabrous stem growth also make this variety an especially attractive shrub;

(9) The anther filaments are colored a very strong shade of vermillion, thereby giving a very striking contrast to the deep lemon yellow open-flower petals, as compared with the much lighter color of the stamen filaments of "Captain Thomas";

(10) Though "Captain Thomas" is highly resistant to mildew, it does frequently develop considerable mildew infection on the peduncles, whereas my new variety is even more resistant to mildew than "Captain Thomas," and rarely ever shows an infection on the peduncles; and

(11) The new variety is completely sterile, and hence sets no hips, as distinguished from the abundant hips and seeds produced by "Captain Thomas" which causes in the parent variety an unsightly appearance, with consequent decrease in flower production in the Fall season.

Asexual reproduction of the new variety by budding at La Canada, California, shows that the foregoing characteristics and distinctions come true to form and are established and transmitted through succeeding propagations.

The accompanying drawings show typical specimens of my new variety, one of said drawings showing in black-and-white a complete plant and depicting its general habits of growth, and the other drawing showing in color typical specimens of the buds, flowers and foliage in different stages of development.

The following is a detailed description of my new variety, as based upon observations of specimens grown at La Canada, California, with color terminology in accordance with Robert F. Wilson's Horticultural Colour Chart, except where general color terms of ordinary dictionary signficance are obvious:

Type: Half-hardy; pillar; outdoor; seedling; for garden decoration.

Class: Hybrid Wichuraiana.

Breeding: Seedling.

*Seed parent.*—"Crimson Glory."

*Pollen parent.*—"Captain Thomas."

Propagation: Holds its distinguishing characteristics through succeeding propagations by budding.

*Flower*

Locality where grown: La Canada, California.

Flowers borne: Several to stem; in irregular cluster; on strong, short stems.

Quantity of bloom: Abundant, outdoors.

Continuity: Continuous.

Fragrance: Moderate; spicy.

Bud:

*Peduncle.*—Short; slender; medium-erect; stiff; medium-green; almost smooth; few small grey hairs.

*Before calyx breaks.* — Size — medium. Form—long; pointed; without foliaceous appendanges on the surface of the bud; with slender foliaceous parts extending beyond the tip of the bud equal to one-half or more of its length; every other sepal having one or two lance-shaped appendages on margins near base, each about ¼ inch long and $\frac{1}{16}$ inch wide. Color—Buttercup Yellow, Plate 5.

*As calyx breaks.—Color*—Buttercup Yellow, Plate 5.

*As first petal opens.* — Size — medium. Form—medium length; pointed. Color—outside: Chrome Yellow, Plate 605; inside: Lemon Yellow, Plate 4. Opening—opens up well, but is retarded from opening by cold weather.

Bloom:

*Size, when fully open.*—Medium; from 3 inches to 3½ inches.

*Petalage.*—Single; 5 petals; arranged regularly; rarely any petaloids.

*Form.*—High-center at first; becoming open to cupped at maturity, but usually flat, with only outer one-quarter of petal curved upward; flowers close up at night and in foggy or cloudy weather.

Petals: Medium thickness; soft; with inside and outside satiny.

*Shape.*—Oval to obovate; apex occasionally having a slight notch.

*Color.*—Remarkably uniform.

This description of a newly opened flower was made from a rose grown outdoors in the month of June at La Canada, California:

*Color.*—Outside petal surface: Chrome Yellow, Plate 605; inside petal surface: Lemon Yellow, Plate 4.

This description was made from a rose that was open for three days outdoors in the month of June at La Canada, California:

*Color.*—Outside petal surface: Empire Yellow, Plate 603 at base, shading to Empire Yellow, Plate 603/1 towards petal tips; inside petal surface: Empire Yellow, Plate 603 at base, shading to Empire Yellow, Plate 603/1 towards petal tips.

*General color effect.*—Empire Yellow, Plate 603/1.

*Behavior.*—Drop off cleanly; fading to very light yellow; fades more rapidly during hot and dry weather.

*Flower longevity.*—On bush in garden—2 days in June. Cut flowers grown outdoors kept at living-room temperatures—2 days in June.

*Reproductive organs*

Stamens: Many; arranged irregularly about pistils; length variable from ¼ inch to ¾ inch.

Filaments: Most with anthers. Color—Near Vermillion, Plate 18.

Anthers: Medium size; open at various times. Color—Lemon Yellow, Plate 4/2, edged with Light Vermillion, Plate 18/2, dots near margins.

Pollen: Abundant. Color—gold.

Pistils: Medium number.

Styles: Very even; very short; medium weight; columnar.

Stigma: Color—almost white.

Ovaries: All enclosed in calyx.

Hips: Does not set hips or seeds.

*Plant*

Foliage:

*Leaves.*—Compound of 3, 5 to occasionally 7 leaflets; very large; thick; leathery; glossy; flat.

*Leaflets.*—Shape—oval, with apex acute; base round; margin simply serrate.

*Color.*—No trace of anthocyanin or red coloring. Mature—upper surface: Near Spinach Green, Plate 0960; under surface: light green. Young—upper surface: normal green; under surface—light green.

*Rachis.*—Medium weight. Upper side—smooth, except for gland-tipped hairs. Under side—extremely smooth, except for 3 or 4 small prickles.

*Stipules.*—Moderately long; very narrow; with medium-length points turning out at an angle of more than 45°.

*Disease.*—Very highly resistant to mildew, as determined by garden observations in comparison with other varieties, and by Petri dish tests in which leaves floating on 10% sugar solution were deliberately infected with mildew spores.

Growth:

*Habit.* — Upright; much-branched; very bushy and compact.

*Growth.*—Vigorous.

*Canes.*—Heavy.

*Main stems.*—Remarkably free of anthocyanin. Color—bright green to very dark green. Thorns—few; medium length; hooked slightly downward; with short, narrow base. Prickles—none. Hairs—none.

*Branches.*—Remarkably free of anthocyanin. Color—bright green. Thorns—few; medium length; hooked downward; with short, narrow base. Prickles — none. Hairs—none.

*New shoots.* — Color — bright green. Thorns—few; medium length; hooked downward; with short, narrow base. Prickles—none. Hairs—none.

I claim:

A new and distinct variety of rose plant of the hybrid Wichuraiana class, substantially as herein shown and described, characterized particularly as to novelty by its bushy and compact habit of growth, by its abundant production of dark green, large, flat and smooth leaves, by its glabrous stem growth and freedom from thorns, by its large, single type flowers and their absence of petaloids, by the uniform deep lemon yellow general color tonality of the flowers, by the dark buttercup yellow color of the buds and their substantially complete freedom of red coloration, by the freedom of anthocyanin pigment in its stems and leaves, by the strong Vermillion color of the anther filaments, and their resultant marked contrast with the color of the open flowers, by the high resistance to mildew of both the foliage and the peduncles, and by its complete sterility and the absence of formation of hips and seeds.

WALTER E. LAMMERTS.

No references cited.